US011603569B2

(12) United States Patent
Essner

(10) Patent No.: US 11,603,569 B2
(45) Date of Patent: Mar. 14, 2023

(54) IMMUNE MODULATING GENES FOR PROGNOSIS, DIAGNOSIS AND TREATMENT OF METASTATIC DISEASE, AND DRUG IDENTIFICATION METHODS THEREOF

(71) Applicant: Cedars-Sinai Medical Center, Los Angeles, CA (US)

(72) Inventor: Richard Essner, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 16/359,636

(22) Filed: Mar. 20, 2019

(65) Prior Publication Data

US 2019/0292604 A1 Sep. 26, 2019

Related U.S. Application Data

(60) Provisional application No. 62/645,688, filed on Mar. 20, 2018.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 8,299,216 B2 * | 10/2012 | Alani | ................. | G01N 33/5743 530/350 |
| 2012/0294872 A1 * | 11/2012 | Gupta | ................. | C12N 15/1137 424/174.1 |
| 2013/0338033 A1 * | 12/2013 | Fisher | .............. | G01N 33/57407 435/7.1 |
| 2020/0283514 A1 * | 9/2020 | Rosser | ................... | C07K 16/24 |

FOREIGN PATENT DOCUMENTS

WO  WO 2016/025717  *  2/2016

OTHER PUBLICATIONS

Erdrich et al. Annals of Surgical Oncology. Feb. 25, 2018. Suppl 1. Abstract 82, p. S39-S40 (Year: 2018).*
Miyake et al Theranostics. Jan. 25, 2019. 9(3): 853-867 (Year: 2019).*
de Oliveira et al. Acta cirurgica Brasileira. 2007. 22(5): 332-336 (Year: 2007).*
Haqq et al PNAS. 2005. 102(17): 6092-6097 and Supporting Table 2 (Year: 2005).*
Singh et al Clin Cancer Res. 2009. 15(7): 2380-2386 (Year: 2009).*
Yang et al. Cancer Research. 2001.61: 4901-4909 (Year: 2001).*
Supplemental Table 3 of Haqq et al PNAS. 2005. 102(17): 6092-6097, 2 pages, available via URL: < pnas.org/content/102/17/6092/tab-figures-data> (Year: 2005).*
Hatano et al Oncotarget, Jul. 2018, 9(57): 31090-31097 (Year: 2018).*
Faries et al., Lymph Node Metastasis in Melanoma: A debate on the significance of nodal metastases, conditional survival analysis and clinical trials, 2018, Clin Exp Metastasis, pp. 1-20.
Booth et al., HDAC inhibitors enhance the immunotherapy response of melanoma cells, 2017, Oncotarget, vol. 8 (47), pp. 83155-83170.
Cristobal et al., Up-regulation of c—Cbl suggests its potential role as oncogene in primary colorectal cancer, 2014, Int. J. Colorectal Dis., vol. 29(5), pp. 641.
Flem-Karlsen et al. Immunoregulatory protein B7—H3 promotes growth and decreases sensitivity to therapy in metastatic melanoma cells., 2017, Pigment Cell Melanoma Res., vol. 30(5), pp. 467-476.
Gershenwald et al., Melanoma Staging: American Joint Committee on Cancer (AJCC) 8th Edition and Beyond In: Ann Surg Oncol., 2018, vol. 25, pp. 2105-2110.
Kadera et al., Low expression of the E3 ubiquitin ligase CBL confers chemoresistance in human pancreatic cancer and is targeted by epidermal growth factor receptor inhibition, 2015, Clin. Cancer Res., vol. 21(1), pp. 157-165.
Kim et al., c—Cbl shRNA-expressing adenovirus sensitizes TRAIL-induced apoptosis in prostate cancer DU-145 through increases of DR4/5, 2013, Cancer Gene Ther., vol. 20(2), pp. 82-87.
Lai et al., Met kinase-dependent loss of the E3 ligase Cbl in gastric cancer, 2012, J. Biol. Chem., vol. 287(11), pp. 8048-8059.
Li et al., Cbl-regulated Akt and ERK signals are involved in beta-elemene-induced cell apoptosis in lung cancer cells, 2011, Mol. Med. Rep., vol. 4(6), pp. 1243-1246.
Liu et al., B7—H3 silencing increases paclitaxel sensitivity by abrogating Jak2/Stat3 phosphorylation, 2011, Mol. Cancer Ther., vol. 10(6), pp. 960-971.
Loo et al., Development of an Fc-enhanced anti-B7—H3 monoclonal antibody with potent antitumor activity, 2012, Clin. Cancer Res., vol. 18(14), pp. 3834-3845.
Nihal et al., c—CBL regulates melanoma proliferation, migration, invasion and the FAK—SRC—GRB2 nexus, 2016, Oncotarget., vol. 7(33), pp. 53869-53880.
Paolino et al., The E3 Ligase Cbl—b and TAM receptors regulate cancer metastasis via natural killer cells, 2014, Nature, vol. 507 (7493), pp. 508-512.
Qu et al., Cbl—b-regulated extracellular signal-regulated kinase signaling is involved in the shikonin-induced apoptosis of lung cancer cells in vitro, 2015, Exp. Ther Med., vol. 9(4), pp. 1265-1270.
Shain et al., Exome sequencing of desmoplastic melanoma identifies recurrent NFKBIE promoter mutations and diverse activating mutations in the MAPK pathway, 2015, Nat. Genet, vol. 47(10), pp. 1194-1199.

(Continued)

*Primary Examiner* — Carla J Myers
(74) *Attorney, Agent, or Firm* — Nixon Peabody LLP; Linda B. Huber

(57) ABSTRACT

Immune-modulating genes are provided for prognosis and diagnosis of metastases or reoccurrence of cancer, as well as methods of prognosis, diagnosis, prophylaxis and treatment of cancer metastases.

14 Claims, 4 Drawing Sheets

(56) References Cited

OTHER PUBLICATIONS

Tan et al., CBL is frequently altered in lung cancers: its relationship to mutations in MET and EGFR tyrosine kinases, 2010, PLoS One. vol. 5(1), pp. e8972.

Taube et al., Differential Expression of Immune-Regulatory Genes Associated with PD—L1 Display in Melanoma Implications for PD-1 Pathway Blockade, 2015, Clin. Cancer Res., vol. 21(17), pp. 3969-3976.

Tekle et al., B7—H3 contributes to the metastatic capacity of melanoma cells by modulation of known metastasis-associated genes, 2012, Int. J. Cancer, vol. 130(10), pp. 2282-2290.

Thurneysen et al., An exploratory study investigating the metabolic activity and local cytokine profile in patients with melanoma treated with pazopanib and paclitaxel, 2016, Br. J. Dermatol., vol. 175(5), pp. 966-978.

Wang et al., B7—H3 associated with tumor progression and epigenetic regulatory activity in cutaneous melanoma, 2013, J. Invest Dermatol., vol. 133(8), pp. 2050-2058.

Young et al., An adaptive signaling network in melanoma inflammatory niches confers tolerance to MAPK signaling Inhibition, 2017, J. Exp. Med., vol. 214(6), pp. 1691-1710.

Guerry IV et al., Lessons from Tumor Progression: The Invasive Radial Growth Phase of Melanoma is Common, Incapable of Metastasis, and Indolent, Invasive Radial Growth-Phase Melanoma, 1993, vol. 100(3), pp. 342S-345S.

Erdrich et al., Four Immune Modulating Genes in Primary Melanoma That Predict Metastatic Potential, Journal of Surgical Research, 2022, vol. 279, pp. 682-691.

NIH RePorter, Surgery and the Mechanisms of Lymph Node Metastases in Cutaneous Melanoma, Award Notice Date: Jul. 21, 2011, Award No. 5R01CA120228-05.

* cited by examiner

IMMUNE MODULATING GENES FOR PROGNOSIS, DIAGNOSIS AND TREATMENT OF METASTATIC DISEASE, AND DRUG IDENTIFICATION METHODS THEREOF

CROSS-REFERENCE TO RELATED APPLICATIONS

This application includes a claim of priority under 35 U.S.C. § 119(e) to U.S. provisional patent application No. 62/645,688, filed Mar. 20, 2018, the entirety of which is hereby incorporated by reference.

STATEMENT REGARDING FEDERALLY SPONSORED RESEARCH OR DEVELOPMENT

This invention was made with Government support under CA120228 awarded by the National Institutes of Health. The Government has certain rights in the invention.

FIELD OF INVENTION

This invention relates to immune modulating genes in the prognosis, diagnosis, drug discovery and/or therapeutic treatment related to metastatic diseases.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Melanoma is the fifth most common cancer for men and the sixth for women in the United States in 2018. Fortunately, nearly 80% of all melanoma cases are diagnosed at an early stage with good survival rates. However, outcomes are markedly worse for patients with metastatic melanoma. Primary melanoma, even when fully excised early, has high rates of metastases. The most recent Cochrane Database reported that five-year survival after a diagnosis of metastatic melanoma is less than 10%. Current methods of staging primary melanoma are based on clinicopathologic features of the primary tumor and sentinel node status. Histologic findings relate to the tumor depth, ulceration, regression and mitotic index, as well as patient age and adjacent lymph node status. These sentinel lymph nodes must be surgically removed and evaluated by pathology, which poses second operative procedure. However, these findings do not always accurately predict which patients will develop distant metastases. There is a pressing need to identify and provide prophylaxis treatment to patients at risk of metastasis before a distant disease develops.

Therefore, it is an objective of the present invention to provide prophylaxis and treatment methods against tumor metastases or metastatic diseases.

It is another objective of the present invention to provide diagnostic markers for determination of treatment effects on patients having had primary tumors and continued treatment methods.

It is yet another objective of the present invention to provide a screening method for drug identification and/or a treatment method for reducing the likelihood of tumor metastases.

SUMMARY OF THE INVENTION

Genetic analysis is shown of selective immunomodulatory genes and their expression patterns in primary tumor specimens for use in identifying subjects at risk of developing distant metastases and prophylactically and/or therapeutically treating these subjects.

Chemokine (C—X—C motif) ligand 1 (CXCL1), chemokine (C—X—C motif) ligand 2 (CXCL2), E3 ubiquitin-protein ligase CBL (CBL), and cluster of differentiation 276 (CD276) are provided as prognostic and diagnostic markers whose overexpression, individually or in combination, in primary tumor are indicative of cancer staging, development of metastatic disease and/or low survival probability of the patients. For example, identification of their statistically significantly increased presence, as a combination of four, a combination of CXCL1 and CXCL2, or singly by CXCL1, in the primary melanoma tumor is used to identify subjects at risk of, or undergoing, development of metastatic disease or melanoma reoccurrence, and to administer therapies such as immunotherapy against these genes or proteins to the identified subjects.

In some embodiments, a detection method of CXCL1 in a subject with tumor is provided including obtaining a biological sample from the subject and detecting the mRNA and/or protein level of CXCL1 in the biological sample of the subject, e.g., with a microarray analysis of the cDNA samples of the subject. Another detection method of CXCL1 is provided including obtaining a biological sample from the subject and detecting whether the mRNA and/or protein level of CXCL1 in the biological sample of the subject is higher, or statistically significantly higher, than a control value (e.g., control value obtained from a healthy or cured subject free of the tumor, or from a subject shown to have not developed metastasis over a time course of 1, 2, 3, 4, 5, 6, 7, 8, 9, 10, or more years). In other embodiments, a diagnosis and/or prognosis method of tumor metastasis is provided including or consisting of (1) detecting the mRNA and/or protein level of CXCL1 in the primary tumor specimen of a subject, e.g., with a microarray analysis of the cDNA samples of the subject and (2) diagnosing or making a prognosis of the subject with tumor metastasis when the mRNA and/or protein level of CXCL1 in the primary tumor specimen of a subject is statistically significantly (p≤0.05) higher compared to a control level (e.g., obtained from a healthy or cured subject free of the tumor). In yet another embodiment, a method of diagnosing and treating tumor metastasis is provided, including or consisting of (1) detecting the mRNA and/or protein level of CXCL1 in the primary tumor specimen of a subject, e.g., with a microarray analysis of the cDNA samples of the subject, (2) diagnosing or making a prognosis of the subject with tumor metastasis when the mRNA and/or protein level of CXCL1 in the primary tumor specimen of a subject is statistically significantly (p≤0.05) higher compared to that of a control level (e.g., obtained from a healthy or cured subject free of the tumor), and (3) administering a therapeutic agent to reduce the expression level of CXCL1 in the subject, so as to treat or reduce the likelihood of metastases.

In additional embodiments, a detection method of CXCL1 and CXCL2 in a subject with tumor is provided including obtaining a biological sample from the subject and detecting the mRNA and/or protein levels of CXCL1 and CXCL2 in the biological sample of the subject, e.g., with a microarray analysis of the cDNA samples of the subject. Another detection method of CXCL1 and CXCL2 is provided including obtaining a biological sample from the subject and detecting whether the mRNA and/or protein levels of CXCL1 and CXCL2 in the biological sample of the subject are higher, or statistically significantly higher, than respective control values (e.g., control value obtained from a healthy or cured subject free of the tumor, or from a subject shown to have not developed metastasis over a time course of 1, 2, 3, 4, 5, 6, 7, 8, 9, 10, or more years). In other embodiments, a diagnosis and/or prognosis method of tumor metastasis is provided including or consisting of (1) detecting the mRNA and/or protein levels of CXCL1 and CXCL2 in the primary tumor specimen of a subject, e.g., with a microarray analysis of the cDNA samples of the subject and (2) diagnosing or making a prognosis of the subject with tumor metastasis when the mRNA and/or protein levels of CXCL1 and CXCL2 in the primary tumor specimen of a subject are each statistically significantly ($p \leq 0.05$) higher compared to respective control levels (e.g., obtained from a healthy or cured subject free of the tumor). In yet another embodiment, a method of diagnosing and treating tumor metastasis is provided, including or consisting of (1) detecting the mRNA and/or protein levels of CXCL1 and CXCL2 in the primary tumor specimen of a subject, e.g., with a microarray analysis of the cDNA samples of the subject, (2) diagnosing or making a prognosis of the subject with tumor metastasis when the mRNA and/or protein levels of CXCL1 and CXCL2 in the primary tumor specimen of a subject are each statistically significantly ($p \leq 0.05$) higher compared to respective control levels (e.g., obtained from a healthy or cured subject free of the tumor), and (3) administering a therapeutic agent to reduce the expression level of CXCL1, optionally further reducing the expression level of CXCL2, in the subject, so as to treat or reduce the likelihood of metastases.

Additional embodiments provide a detection method of CXCL1, CXCL2, EBL and CD276 in a subject with tumor is provided including obtaining a biological sample from the subject and detecting the mRNA and/or protein levels of CXCL1, CXCL2, EBL and CD276 in the biological sample of the subject, e.g., with a microarray analysis of the cDNA samples of the subject. Another detection method of CXCL1, CXCL2, EBL and CD276 is provided including obtaining a biological sample from the subject and detecting whether the mRNA and/or protein levels of CXCL1, CXCL2, EBL and CD276 in the biological sample of the subject are higher, or statistically significantly higher, than respective control values (e.g., control value obtained from a healthy or cured subject free of the tumor, or from a subject shown to have not developed metastasis over a time course of 1, 2, 3, 4, 5, 6, 7, 8, 9, 10, or more years). In other embodiments, a diagnosis and/or prognosis method of tumor metastasis is provided including or consisting of (1) detecting the mRNA and/or protein levels of CXCL1, CXCL2, CBL and CD276 in the primary tumor specimen of a subject, e.g., with a microarray analysis of the cDNA samples of the subject, and (2) diagnosing or making a prognosis of the subject with tumor metastasis when the mRNA and/or protein levels of CXCL1, CXCL2, CBL and CD276 in the primary tumor specimen of a subject are each statistically significantly ($p \leq 0.05$) higher compared to respective control levels (e.g., obtained from a healthy or cured subject free of the tumor). In yet another embodiment, a method of diagnosing and treating tumor metastasis is provided, including or consisting of (1) detecting the mRNA and/or protein levels of CXCL1, CXCL2, CBL and CD276 in the primary tumor specimen of a subject, e.g., with a microarray analysis of the cDNA samples of the subject, (2) diagnosing or making a prognosis of the subject with tumor metastasis when the mRNA and/or protein levels of CXCL1, CXCL2, CBL and CD276 in the primary tumor specimen of a subject are each statistically significantly ($p \leq 0.05$) higher compared to respective control levels (e.g., obtained from a healthy or cured subject free of the tumor), and (3) administering a therapeutic agent to reduce the expression level of CXCL1, optionally further reducing the expression levels of CXCL2, CBL and CD276 in the subject, so as to treat or reduce the likelihood of metastases.

In some aspects, the cancer in the method is melanoma, and the elevated expression levels are compared to one or more control levels, e.g., value(s) or averaged value(s) (from a pool of individuals) obtained from subjects free from melanoma, from tissue samples free from melanoma, or from melanoma samples of subjects that do not have metastases or reoccurrence of melanoma. In some aspects, the elevated expression levels are: (1) CXCL1 has a differential expression fold change (DEFC) of about 2.51, (2) CXCL1 has a DEFC of about 2.51 and CXCL2 has a DEFC of about 1.68, or (3) CXCL1 has a DEFC of about 2.51, CXCL2 has a DEFC of about 1.68, CBL has a DEFC of about 1.15, and CD276 has a DEFC of about 1.16, compared to the averaged value(s) obtained from melanoma samples of subjects that do not have metastases or reoccurrence of the cancer. In other aspects, the elevated expression levels are: (1) CXCL1 has a differential expression fold change (DEFC) of at least 2.51, (2) CXCL1 has a DEFC of at least 2.51 and CXCL2 has a DEFC of at least 1.68, or (3) CXCL1 has a DEFC of at least 2.51, CXCL2 has a DEFC of at least 1.68, CBL has a DEFC of at least 1.15, and CD276 has a DEFC of at least 1.16, compared to the averaged value(s) obtained from melanoma samples of subjects that do not have metastases or reoccurrence of the cancer.

In further aspects, the therapeutic agent to treat, reduce the likelihood or severity of, or slow the progression of metastases or reoccurrence of melanoma includes an inhibitor of one or more of CXCL1, CXCL2, CBL and CD276, or an inhibitor of the receptor(s) of CXCL1, CXCL2 and/or CD276.

In other embodiments, a method of treatment of melanoma in subjects unlikely to develop metastases or reoccurrence of melanoma includes local removal of the melanoma tissue, where the levels of CXCL1, CXCL2, CBL (an E3 ubiquitin-protein ligase) and CD276 are similar to respective control levels (e.g., from subjects free from melanoma, from tissue samples free from melanoma, or from melanoma samples of subjects that do not have metastases or reoccurrence of melanoma). In further aspects, no further treatment such as radiation, immunotherapy, chemotherapy, or surgical lymph node biopsy is performed in subject so identified as unlikely to develop metastases or reoccurrence of melanoma.

Elevated expressions of interleukin 1 alpha (IL1A) and receptor-type tyrosine-protein phosphatase kappa (protein-tyrosine phosphatase kappa, PTPRK), in combination with elevated Clark's Level, from a melanoma sample are also provided as prognostic and diagnostic markers of identifying lymph node metastases. In various other embodiments, a method is provided of detecting and treating, reducing the likelihood or severity of, or slowing the progression of lymph node metastases in a subject with melanoma, including detecting elevated expression levels of IL1A and PTPRK, and detecting elevated Clark's Level, in a melanoma sample from the subject; and administering a therapeutically effective amount of a therapeutic agent to the subject to reduce, inhibit or block the expression and/or function of IL1A and PTPRK, thereby treating, reducing the likelihood or severity of, or slowing the progression of lymph node metastases. In further aspects, the elevated expression levels and elevated Clark's Level are compared to the control levels, e.g., averaged values obtained from subjects free from melanoma or from melanoma samples of subjects that do not have lymph node metastases.

Using microarray analysis of cDNA samples from primary tumor, immunomodulatory genes with high sensitivity and specificity to predict metastatic potential are identified. For a patient having completed biopsy or excision, generally no additional invasive procedures are needed, as the primary tumor samples can be analyzed for prognosis of metastatic potential.

Microarray analysis of primary tumor is also provided. This method is not routine or currently used in existing algorithms of selecting patients for surveillance and treatment. In some embodiments, microarray analysis of gene expression profiles is performed on fresh biological samples. In other embodiments, microarray analysis of gene expression profiles is performed on paraffin-embedded biological samples. Generally, the microarray analysis of primary tumor samples includes hybridizing detectably labeled RNA of the biological sample in an oligonucleotide microarray chip, wherein the oligonucleotide microarray chip contains one or more oligonucleotides that bind target genes, and quantifying the RNA amount of target genes in the biological sample via the detectable label. For example, a method is provided of identifying subjects who have a primary tumor, e.g., melanoma, and are at risk or already have metastases by performing microarray analysis on the sample from the primary tumor to identify elevated expressions of (1) a combination of CXCL1, CXCL2, CBL and CD276; (2) a combination of CXCL1 and CXCL2, or (3) CXCL1, compared to averaged value(s) obtained from subjects free from melanoma, from tissue samples free from melanoma, or from melanoma samples of subjects that do not have metastases or reoccurrence of melanoma.

A method of identifying an agent to reduce the activity or expression of CXCL1 is provided, including contacting a candidate agent with a biological sample (e.g., tumor sample), detecting the activity or expression level of CXCL1 in the biological sample, and determining the candidate agent is an agent that reduces the activity of expression of CXCL1 when the activity or expression level of CXCL1 is decreased after the contact. Also provided is a process of identifying candidate agents and using them for treating, reducing the likelihood or severity of, or slowing the progression of metastases or reoccurrence of melanoma, including detecting a reduction induced by a candidate agent after contact with a biological sample, preferably a melanoma tissue sample or a melanoma cell line, in the activity, the transcription level or the expression level of one or more of CXCL1, CXCL2, CBL and CD276, or of their receptors, compared to that or those of the biological sample before the contact, and administering the candidate agent to a subject having melanoma or symptoms of melanoma.

The following embodiments and aspects thereof are described and illustrated in conjunction with compositions and methods which are meant to be exemplary and illustrative, not limiting in scope.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
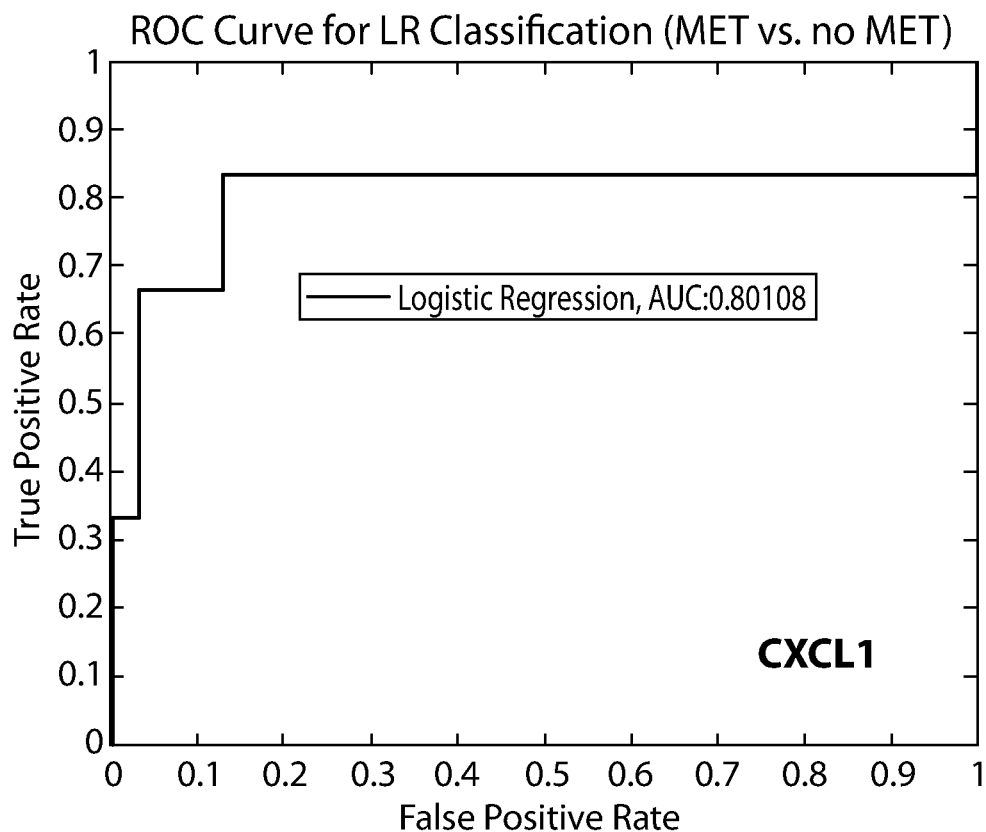
FIGS. 1 and 2 depict the receiver operating characteristic curve (ROC curve) for CXCL1 (FIG. 1) and CXCL2 (FIG. 2), respectively.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed, Revised, J. Wiley & Sons (New York, N.Y. 2006); March, *Advanced Organic Chemistry Reactions, Mechanisms and Structure* $7^{th}$ ed., J. Wiley & Sons (New York, N.Y. 2013); and Sambrook and Russel, *Molecular Cloning: A Laboratory Manual* $4^{th}$ ed., Cold Spring Harbor Laboratory Press (Cold Spring Harbor, N.Y. 2012), provide one skilled in the art with a general guide to many of the terms used in the present application. For references on how to prepare antibodies, see D. Lane, *Antibodies: A Laboratory Manual* $2^{nd}$ ed. (Cold Spring Harbor Press, Cold Spring Harbor N.Y., 2013); Kohler and Milstein, (1976) Eur. J. Immunol. 6: 511; Queen et al. U.S. Pat. No. 5,585,089; and Riechmann et al., Nature 332: 323 (1988); U.S. Pat. No. 4,946,778; Bird, Science 242:423-42 (1988); Huston et al., Proc. Natl. Acad. Sci. USA 85:5879-5883 (1988); Ward et al., Nature 334:544-54 (1989); Tomlinson I. and Holliger P. (2000) Methods Enzymol, 326, 461-479; Holliger P. (2005) Nat. Biotechnol. September; 23(9):1126-36).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Sample" or "biological sample" as used herein generally refers to tissues or body fluids removed from a mammal or cell/tissue cultures that grow from the tissue or body fluids removed from the mammal. Various embodiments provide the biological sample from a subject who has or has had symptoms of a cancer refers to the cancerous tissue or tumor-containing body fluids, with which a detection of gene/protein expression levels including that of CXCL1 is performed and can be compared with respective control levels. Samples can be blood and/or blood fractions, including peripheral blood sample like peripheral blood mononuclear cell (PBMC) sample or blood (e.g., whole blood, plasma, serum), bone marrow cell sample, or cerebral spinal fluid (CSF). Samples can also be a biopsy of tissue. A sample can also include, without limitation, lymphoid, thymus, pancreas, eye, heart, liver, nerves, intestine, skin, muscle, cartilage, ligament, synovial fluid, and/or joints. The samples can also be taken from any individual including a healthy individual or an individual having cells, tissues, and/or an organ afflicted with a tumor, such as melanoma. They include but are not limited to drawing and processing blood and blood components, or obtaining biopsies from the bone marrow or other tissues or organs, or primary tumor sites, or secondary tumor sites using standard medical techniques. In some embodiments, the sample (e.g., tissues or cells) is obtained by needle biopsy. In some embodiments, a method is provided using a needle biopsy to obtain tissue samples for detection and diagnosis of tumor metastasis by analyzing gene expressions.

The terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

A "cancer" or "tumor" as used herein refers to an uncontrolled growth of cells which interferes with the normal functioning of the bodily organs and systems, and/or all neoplastic cell growth and proliferation, whether malignant or benign, and all pre-cancerous and cancerous cells and tissues. A subject that has a cancer or a tumor is a subject having objectively measurable cancer cells present in the subject's body. Included in this definition are benign and malignant cancers, as well as dormant tumors or micrometastasis (generally undetectable by standard methods). "Metastasis" generally refers to the spreading of cancer from its primary site to secondary sites, which is a multi-step process that typically involves loss of cell adhesion, increased cell motility, invasion of the surrounding tissue, intravasation of blood vessels or the lymphatic system to enter the circulatory system, extravasation from the circulatory system, proliferation at a new secondary site, and building of a vascular system to support growth. Cancers which migrate from their original location and seed vital organs can eventually lead to the death of the subject through the functional deterioration of the affected organs. While primary tumors can normally be removed by surgery, widely metastatic lesions are difficult to detect and difficult or impossible to treat with adjuvant therapies. The term "invasive" refers to the ability to infiltrate and destroy surrounding tissue. Typically doctors give a metastasis the same name as the original cancer. For example, a breast cancer that spreads to the liver is referred to as "metastatic breast cancer," but metastases may differ from the primary (original) tumor at the molecular and genetic level. Examples of cancer include, but are not limited to melanoma, nervous system tumor, B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, head and neck cancer, brain cancer, and prostate cancer, including but not limited to androgen-dependent prostate cancer and androgen-independent prostate cancer.

The term "administering," refers to the placement of an agent as disclosed herein into a subject by a method or route which results in at least partial localization of the agents at a desired site. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intracranial, intraventricular, intrathecal, epidural, intradural, intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, sub capsular, cutaneous, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein.

A "subject" means a human or animal. Usually the animal is a vertebrate such as a primate, rodent, domestic animal or game animal. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

The term "statistically significant" or "significantly" refers to statistical evidence that there is a difference. It is defined as the probability of making a decision to reject the null hypothesis when the null hypothesis is actually true. The decision is often made using the p-value.

The term "average" value generally refers to the arithmetic mean, the sum of the numbers divided by how many numbers are being averaged. In some embodiments, it refers to the median, the middle point of a number set, in which half the numbers are above the median and half are below.

Gene Markers

One or more immune-modulatory genes present in tumor tissues, and the combination thereof, are provided whose upregulation is indicative of metastasis, high likelihood of metastasis, and/or low 5-year survival outcome of subjects, where the genes or the proteins expressed therefrom include chemokine (C—X—C motif) ligand 1 (CXCL1), chemokine (C—X—C motif) ligand 2 (CXCL2), E3 ubiquitin-protein ligase CBL, and cluster of differentiation 276 (CD276).

Detection Methods

In some embodiments, a detection method of CXCL1 in a subject with tumor is provided including obtaining a biological sample from the subject and detecting the mRNA and/or protein level of CXCL1 in the biological sample of the subject, e.g., with a microarray analysis of the cDNA samples of the subject.

Another detection method of CXCL1 is provided including obtaining a biological sample from the subject and detecting whether the mRNA and/or protein level of CXCL1 in the biological sample of the subject is higher, or statistically significantly higher, than a control value (e.g., control value obtained from a healthy or cured subject free of the tumor, or from a subject shown to have not developed metastasis over a time course of 1, 2, 3, 4, 5, 6, 7, 8, 9, 10, or more years).

In additional embodiments, a detection method of CXCL1 and CXCL2 in a subject with tumor is provided including obtaining a biological sample from the subject and detecting the mRNA and/or protein levels of CXCL1 and CXCL2 in the biological sample of the subject, e.g., with a microarray analysis of the cDNA samples of the subject.

Another detection method of CXCL1 and CXCL2 is provided including obtaining a biological sample from the subject and detecting whether the mRNA and/or protein levels of CXCL1 and CXCL2 in the biological sample of the subject are higher, or statistically significantly higher, than respective control values (e.g., control value obtained from a healthy or cured subject free of the tumor, or from a subject shown to have not developed metastasis over a time course of 1, 2, 3, 4, 5, 6, 7, 8, 9, 10, or more years).

Additional embodiments provide a detection method of CXCL1, CXCL2, EBL and CD276 in a subject with tumor is provided including obtaining a biological sample from the subject and detecting the mRNA and/or protein levels of CXCL1, CXCL2, EBL and CD276 in the biological sample of the subject, e.g., with a microarray analysis of the cDNA samples of the subject.

Another detection method of CXCL1, CXCL2, EBL and CD276 is provided including obtaining a biological sample from the subject and detecting whether the mRNA and/or protein levels of CXCL1, CXCL2, EBL and CD276 in the biological sample of the subject are higher, or statistically significantly higher, than respective control values (e.g., control value obtained from a healthy or cured subject free of the tumor, or from a subject shown to have not developed metastasis over a time course of 1, 2, 3, 4, 5, 6, 7, 8, 9, 10, or more years).

Diagnosis and/or Prognosis

In some embodiments, a diagnosis and/or prognosis method of tumor metastasis is provided including or consisting of (1) detecting the mRNA and/or protein level of CXCL1 in the primary tumor specimen of a subject, e.g., with a microarray analysis of the cDNA samples of the subject and (2) diagnosing or making a prognosis of the subject with tumor metastasis when the mRNA and/or protein level of CXCL1 in the primary tumor specimen of a subject is statistically significantly ($p \leq 0.05$) higher compared to a control level (e.g., obtained from a healthy or cured subject free of the tumor).

In other embodiments, a diagnosis and/or prognosis method of tumor metastasis is provided including or consisting of (1) detecting the mRNA and/or protein levels of CXCL1 and CXCL2 in the primary tumor specimen of a subject, e.g., with a microarray analysis of the cDNA samples of the subject and (2) diagnosing or making a prognosis of the subject with tumor metastasis when the mRNA and/or protein levels of CXCL1 and CXCL2 in the primary tumor specimen of a subject are each statistically significantly ($p \leq 0.05$) higher compared to respective control levels (e.g., obtained from a healthy or cured subject free of the tumor).

In other embodiments, a diagnosis and/or prognosis method of tumor metastasis is provided including or consisting of (1) detecting the mRNA and/or protein levels of CXCL1, CXCL2, CBL and CD276 in the primary tumor specimen of a subject, e.g., with a microarray analysis of the cDNA samples of the subject, and (2) diagnosing or making a prognosis of the subject with tumor metastasis when the mRNA and/or protein levels of CXCL1, CXCL2, CBL and CD276 in the primary tumor specimen of a subject are each statistically significantly ($p \leq 0.05$) higher compared to respective control levels (e.g., obtained from a healthy or cured subject free of the tumor).

In various embodiments, a method of prognosis of metastatic disease or determining the likelihood of tumor reoccurrence is provided by measuring the level(s) of (1) CXCL1; of (2) both CXCL1 and CXCL2; or of (3) each in the combination of CXCL1, CXCL2, CBL and CD276, from a primary tumor sample of a subject, where increased level(s) of the one, two, or four markers, respectively, indicate the subject is at risk of developing metastases or tumor reoccurrence.

In further embodiments, a subject at risk of developing metastases or tumor reoccurrence has differential expression fold change (DEFC) of 2.51 for CXCL1, compared to control; 2.51 for CXCL1 and 1.68 for CXCL2, compared to control; or 2.51 for CXCL1, 1.68 for CXCL2, 1.15 for CBL, and 1.16 for CD276, compared to control. Another aspect provides a subject at risk of developing metastases or tumor reoccurrence has differential expression fold change (DEFC) of about 2.51 for CXCL1, compared to control; about 2.51 for CXCL1 and about 1.68 for CXCL2, compared to control; or about 2.51 for CXCL1, about 1.68 for CXCL2, about 1.15 for CBL, and about 1.16 for CD276, compared to control. Yet another aspect provides a subject at risk of developing metastases or tumor reoccurrence has differential expression fold change (DEFC) of at least 2.51 for CXCL1, compared to control; at least 2.51 for CXCL1 and at least 1.68 for CXCL2, compared to control; or at least 2.51 for CXCL1, at least 1.68 for CXCL2, at least 1.15 for CBL, and at least 1.16 for CD276, compared to control. In another embodiment, a subject at risk of developing metastases or tumor reoccurrence has level(s) of CXCL1 more than 150% greater than control; CXCL1 more than 150% and CXCL2 more than 60% greater than control; or CXCL1 more than 150%, CXCL2 more than 60%, CBL more than 10% and CD276 more than 10% greater than control. In these embodiments, control refers to the level(s) of the genes from a subject free from melanoma, from a tissue sample free from melanoma, or from the primary melanoma tissue of a subject that does not have melanoma reoccurrence and metastatic disease after local melanoma excision.

In some further aspects, a subject at risk of developing metastases or tumor reoccurrence has differential expression fold change (DEFC) of about 2.50 fold, 2.75 fold, 3.00 fold, 3.25 fold or 3.50 fold, or more, for CXCL1, compared to control; about 2.50 fold, 2.75 old, 3.00 fold, 3.25 fold or 3.50 fold, or more, for CXCL1 and about 1.60 fold, 1.65 fold, 1.70 fold, 1.75 fold or 2.00 fold, or more, for CXCL2, compared to control; or about 2.50 fold, 2.75 fold, 3.00 fold, 3.25 fold or 3.50 fold, or more, for CXCL1, about 1.60 fold, 1.65 fold, 1.70 fold, 1.75 fold or 2.00 fold, or more, for CXCL2, about 1.10 fold, 1.15 fold, 1.20 fold or 1.25 fold, or more, for CBL, and about 1.10 fold, 1.15 fold, 1.20 fold or 1.25 fold, or more, for CD276.

In various embodiments, a method of prognosis of metastatic melanoma or determining the likelihood of melanoma reoccurrence is provided by quantifying the level(s) of CXCL1; of both CXCL1 and CXCL2; or of the combination of CXCL1, CXCL2, CBL and CD276, from a primary melanoma tissue sample of a subject, where increased level(s) of the one, two, or four markers, respectively, indicate the subject is at risk of developing melanoma metastases or reoccurrence.

In another embodiment, a subject at risk of developing melanoma metastases or reoccurrence has differential expression fold change (DEFC) of about 2.51 for CXCL1, compared to control subject's; about 2.51 for CXCL1 and about 1.68 for CXCL2, compared to control subject's; or about 2.51 for CXCL1, about 1.68 for CXCL2, about 1.15 for CBL, and about 1.16 for CD276, compared to control subject's; where control is the value(s) of respective genes or proteins from a subject free from melanoma, from a tissue sample free from melanoma of a subject, or from the primary melanoma tissue of a subject that does not have melanoma reoccurrence and metastatic disease after local melanoma excision.

In some aspects, CXCL1 in the primary melanoma specimen of a subject at risk of developing metastatic disease or melanoma reoccurrence is upregulated in an amount of about 1.5, 2.0, 2.5, 3.0, 3.5 or 4.0 fold change, or more, compared to that in a control subject; CXCL2 in the primary melanoma specimen of a subject at risk of developing metastatic disease or melanoma reoccurrence is upregulated in an amount of about 1.3, 1.4, 1.5, 1.6, 1.7, 1.8, 1.9, 2.0, 2.1, 2.2, 2.3, 2.4, 2.5, or 3.0 fold change, or more, compared to that in a control subject; CBL in the primary melanoma specimen of a subject at risk of developing metastatic disease or melanoma reoccurrence is upregulated in an amount of about 1.1, 1.15, 1.2, 1.3, 1.4, 1.5, or 2-fold change, or more, compared to that in a control subject; and CD276 in the primary melanoma specimen of a subject at risk of developing metastatic disease or melanoma reoccurrence is upregulated in an amount of about 1.1, 1.16, 1.2, 1.3, 1.4, 1.5, or 2- fold change, or more, compared to that in a control subject.

In other aspects, CXCL1 in the primary melanoma specimen of a subject at risk of developing metastatic disease or melanoma reoccurrence is upregulated in an amount of about 2.50 fold, or at least 2.50 fold 2.75 fold, 3.00 fold, 3.25 fold or 3.50 fold, compared to that in a control subject; CXCL2 in the primary melanoma specimen of a subject at risk of developing metastatic disease or melanoma reoccurrence is upregulated as in an amount of about 1.68 fold, or at least 1.60 fold, 1.65 fold, 1.70 fold, 1.75 fold or 2.00 fold, compared to that in a control subject; CBL in the primary melanoma specimen of a subject at risk of developing metastatic disease or melanoma reoccurrence is upregulated as in an amount of about 1.15 fold, or at least 1.10 fold, 1.15 fold, 1.20 fold or 1.25 fold, compared to that in a control subject; and CD276 in the primary melanoma specimen of a subject at risk of developing metastatic disease or melanoma reoccurrence is upregulated in an amount of about 1.16 fold, or at least 1.10 fold, 1.15 fold, 1.20 fold or 1.25 fold, compared to that in a control subject.

In various embodiments, the upregulation of both IL1A and PTPRK, in combination of an increased ClarkLevel, in the primary tumor tissue of a subject, compared to a reference value or a control, determines a high likelihood of the subject or the subject is at risk of metastases. Clark's level (also denoted herein as ClarkLevel) is a staging system, used in conjunction with Breslow's depth, which describes the level of anatomical invasion of the melanoma in the skin, as known in the art. Clark level and Breslow depth are determined by a pathologist evaluation of the tissue specimen using a microscope.

In further embodiments, the upregulation of both IL1A and PTPRK in the primary tissue of a subject, compared to a reference value or a control, in combination of an increased ClarkLevel, determines a high likelihood of the subject or the subject is at risk of developing lymph node metastases.

In various embodiments, a method of prognosis of lymph node metastasis includes measuring the level(s) of ACTA2, or the combination of IL1A, PTPRK and ClarkLevel, of a subject, where increased level(s) of the one or the three markers, respectively, indicate the subject is at a high risk of developing lymph node metastasis. In some embodiments, a subject at risk of developing lymph node metastases according to the prognosis method above further undergo sentinel lymph node biopsy. Some embodiments provide the method for prognosis does not include determining the serum level of S-100.

In various embodiments, the methods above keep patients from being overtreated or undertreated, which lowers the morbidity and mortality of the patients.

Therapeutic and/or Prophylactic Treatment

A method of diagnosing and treating tumor metastasis is provided, including or consisting of (1) detecting the mRNA and/or protein level of CXCL1 in the primary tumor specimen of a subject, e.g., with a microarray analysis of the cDNA samples of the subject, (2) diagnosing or making a prognosis of the subject with tumor metastasis when the mRNA and/or protein level of CXCL1 in the primary tumor specimen of a subject is statistically significantly ($p \leq 0.05$) higher compared to that of a control level (e.g., obtained from a healthy or cured subject free of the tumor), and (3) administering a therapeutic agent to reduce the expression level of CXCL1 in the subject, so as to treat or reduce the likelihood of metastases.

In yet another embodiment, a method of diagnosing and treating tumor metastasis is provided, including or consisting of (1) detecting the mRNA and/or protein levels of CXCL1 and CXCL2 in the primary tumor specimen of a subject, e.g., with a microarray analysis of the cDNA samples of the subject, (2) diagnosing or making a prognosis of the subject with tumor metastasis when the mRNA and/or protein levels of CXCL1 and CXCL2 in the primary tumor specimen of a subject are each statistically significantly ($p \leq 0.05$) higher compared to respective control levels (e.g., obtained from a healthy or cured subject free of the tumor), and (3) administering a therapeutic agent to reduce the expression level of CXCL1, optionally further reducing the expression level of CXCL2, in the subject, so as to treat or reduce the likelihood of metastases.

In yet another embodiment, a method of diagnosing and treating tumor metastasis is provided, including or consisting of (1) detecting the mRNA and/or protein levels of CXCL1, CXCL2, CBL and CD276 in the primary tumor specimen of a subject, e.g., with a microarray analysis of the cDNA samples of the subject, (2) diagnosing or making a prognosis of the subject with tumor metastasis when the mRNA and/or protein levels of CXCL1, CXCL2, CBL and CD276 in the primary tumor specimen of a subject are each statistically significantly ($p \leq 0.05$) higher compared to respective control levels (e.g., obtained from a healthy or cured subject free of the tumor), and (3) administering a therapeutic agent to reduce the expression level of CXCL1, optionally further reducing the expression levels of CXCL2, CBL and CD276 in the subject, so as to treat or reduce the likelihood of metastases.

In various embodiments, a method for identifying and treating subjects having developed or having a high likelihood of developing metastasis, wherein the subject has a primary tumor, includes or consists of detecting upregulation in the mRNA level, the protein level, or both, of (1) CXCL1; (2) each of CXCL1 and CXCL2; or (3) each in the combination of CXCL1, CXCL2, CBL and CD276, in the primary tumor tissue of a subject, compared to a reference value or a control, and directing the subject with a high likelihood or at risk of developing, or having developed metastases to one or more treatments. A further aspect of the method provides administering a therapeutic agent to the identified subject with a high likelihood or at risk of developing, or having developed metastases, wherein the therapeutic agent reduces the mRNA level, the protein level, or both, of (1) CXCL1; (2) each of CXCL1 and CXCL2; or (3) each in the combination of CXCL1, CXCL2, CBL and CD276.

In some embodiments, a subject at risk of developing metastases or tumor reoccurrence according to the prognosis method above further undergo targeted immunotherapy.

In various embodiments, a method of treating cutaneous melanoma and inhibiting or reducing the likelihood of melanoma reoccurrence or metastases includes (a) quantifying the level(s) of CXCL1; of both CXCL1 and CXCL2; or of the combination of CXCL1, CXCL2, CBL and CD276, from a primary melanoma tissue of a subject; and (b) performing local excision of cutaneous melanoma on the subject, if the level(s) of CXCL1 is within 150% difference from control; CXCL1 within 150% and CXCL2 within 60% difference from control; or CXCL1 within 150%, CXCL2 within 60%, CBL within 10% and CD276 within 10% difference from control. In these embodiments, control refers to the level(s) of the genes from a subject free from melanoma, from a tissue sample free from melanoma, or from the primary melanoma tissue of a subject that does not have melanoma reoccurrence and metastatic disease after local melanoma excision.

In further embodiments, the upregulation of (1) CXCL1; (2) each of CXCL1 and CXCL2; or (3) each in the combination of CXCL1, CXCL2, CBL and CD276, in the primary melanoma tissue of a subject, compared to a reference value or a control, determines a high likelihood of the subject or the subject has developed metastatic disease or melanoma reoccurrence even after primary melanoma excision.

In various embodiments, a method of therapeutic intervention is provided including administering a therapeutically effective amount of one or more inhibitors of CXCL1, CXCL2, CBL and CD276, or inhibitors of their receptors, to a subject identified as having a high likelihood or at risk of developing metastases or tumor reoccurrence by methods of the present invention.

In some embodiments, a method of therapeutic intervention is provided including administering a therapeutically effective amount of one or more inhibitors of CXCL1, CXCL2, CBL and CD276, or inhibitors of their receptors, to a subject identified as having a high likelihood or at risk of developing metastases or tumor reoccurrence; and measuring the mRNA, protein, or both, expression level(s) of (1) CXCL1; (2) each of CXCL1 and CXCL2; or (3) each of CXCL1, CXCL2, CBL and CD276, after the administration, wherein decreased level(s) compared to before the administration or similar level(s) to those of a control subject indicates success of therapeutic intervention.

In further aspects, the subject identified as having a high likelihood or at risk of developing metastases or tumor reoccurrence has differential expression fold change (DEFC) of about 2.51 for CXCL1, compared to control; about 2.51 for CXCL1 and about 1.68 for CXCL2, compared to control; or about 2.51 for CXCL1, about 1.68 for CXCL2, about 1.15 for CBL, and about 1.16 for CD276, compared to control; where control is the averaged value(s) from subjects free from melanoma, from tissue samples free from melanoma of subjects, or from the primary melanoma tissue of subjects that do not have melanoma reoccurrence and metastatic disease after local melanoma removal.

In some further aspects, the subject identified as having a high likelihood or at risk of developing metastases or tumor reoccurrence has differential expression fold change (DEFC) of about 2.50 fold, 2.75 fold, 3.00 fold, 3.25 fold or 3.50 fold, or more, for CXCL1, compared to control; about 2.50 fold, 2.75 old, 3.00 fold, 3.25 fold or 3.50, or more, fold for CXCL1 and about 1.60 fold, 1.65 fold, 1.70 fold, 1.75 fold or 2.00 fold, or more, for CXCL2, compared to control; or about 2.50 fold, 2.75 fold, 3.00 fold, 3.25 fold or 3.50 fold, or more, for CXCL1, about 1.60 fold, 1.65 fold, 1.70 fold, 1.75 fold or 2.00 fold, or more, for CXCL2, about 1.10 fold, 1.15 fold, 1.20 fold or 1.25 fold, or more, for CBL, and about 1.10 fold, 1.15 fold, 1.20 fold or 1.25 fold, or more, for CD276.

In some embodiments, a method for identification and therapeutic treatment of a subject having metastatic disease or a high likelihood thereof includes measuring the level(s) of (1) CXCL1; (2) each CXCL1 and CXCL2; or (3) each in the combination of CXCL1, CXCL2, CBL and CD276, from a primary tumor sample of a subject, to identify the subject according to increased level(s) of above, compared to a control; and administering a therapeutically effective amount of one or more inhibitors of CXCL1, CXCL2, CBL and CD276 to the subject.

In some embodiments, a method for identification and therapeutic treatment of a subject having metastatic disease or melanoma reoccurrence, or a high likelihood thereof, includes measuring the level(s) of (1) CXCL1; (2) each of CXCL1 and CXCL2; or (3) each in the combination of CXCL1, CXCL2, CBL and CD276, from a primary melanoma sample of a subject, to identify the subject according to increased level(s) of above, compared to a control; and administering a therapeutically effective amount of one or more inhibitors of CXCL1, CXCL2, CBL and CD276 to the subject.

In further aspects, the subject identified as having metastatic disease or melanoma reoccurrence, or a high likelihood thereof, has differential expression fold change (DEFC) of 2.51 or more for CXCL1, compared to control; 2.51 or more for CXCL1 and 1.68 or more for CXCL2, compared to control; or 2.51 or more for CXCL1, 1.68 or more for CXCL2, 1.15 or more for CBL, and 1.16 or more for CD276, compared to control; where control is the averaged value(s) from subjects free from melanoma, from tissue samples free from melanoma of subjects, or from the primary melanoma tissue of subjects that do not have melanoma reoccurrence and metastatic disease after local melanoma removal.

In other embodiments, a method for identification and surgical treatment of a subject with primary melanoma but not at risk of developing metastatic disease or melanoma reoccurrence, includes measuring the level(s) of (1) CXCL1; (2) each CXCL1 and CXCL2; or (3) each in the combination of CXCL1, CXCL2, CBL and CD276, from a primary melanoma sample of a subject, to identify the subject according to similar level(s) of above, compared to a control; and performing surgical procedure to remove the melanoma tissue. In further aspects, the similar level(s) are when CXCL1 is within 150% difference from control; CXCL1 within 150% and CXCL2 within 60% difference from control; and CXCL1 within 150%, CXCL2 within 60%, CBL within 10% and CD276 within 10% difference from control.

In other embodiments, a method surgical treatment of a subject with primary melanoma but not at risk of developing metastatic disease or melanoma reoccurrence, includes performing surgical procedure to remove the melanoma tissue in a subject whose level(s) of (1) CXCL1; (2) each CXCL1 and CXCL2; or (3) each in the combination of CXCL1, CXCL2, CBL and CD276, from a primary melanoma sample of a subject, have been measured and identified as not having a high likelihood of metastasis.

In various embodiments, the inhibitor of CXCL1 or its receptor is a small molecule or an antibody or a fragment thereof, or a nucleic acid. Exemplary inhibitors of CXCL1 or its receptor include repertaxin, ladarixin, an antibody or an antigen-binding fragment thereof (e.g., monoclonal antibodies raised to block the function of CXCL1 including HL2401), or a nucleic acid cleaving the mRNA of CXCL1.

In various embodiments, the inhibitor of CXCL2 or its receptor is a small molecule or an antibody or a fragment thereof, or a nucleic acid. Exemplary inhibitors of CXCL2 or its receptor include AZD5069, Cpd 19 (3-(2-(cyclopentylamino)-3,4-dioxocyclobut-1-enylamino)-2-hydroxy-N, N-dimethylbenzamide), Sch-527123 (also known as MK-7123), SB272844, SB-656933, an antibody or an antigen-binding fragment thereof, or a nucleic acid cleaving the mRNA of CXCL2.

In various embodiments, the inhibitor of CBL is a small molecule or an antibody or a fragment thereof, or a nucleic acid. Exemplary inhibitors of CBL include P0057390, P0087798 and P0057390.

In various embodiments, the inhibitor of CD276 is a small molecule or an antibody or a fragment thereof, or a nucleic acid. Exemplary inhibitors of CD276 include anti-CD276 antibodies such as enoblituzumab.

In various embodiments, the method of therapeutic intervention or treatment above further includes administering existing therapy for tumor treatment. Exemplary existing treatment for melanoma includes a lymph node dissection if cancer cells are found in the adjacent sentinel lymph node biopsy (controversial); adjuvant treatment with immunotherapy (such as pembrolizumab, nivolumab, ipilimumab, or interferon) or targeted therapy; radiation therapy; Talimogene laherparepvec/T-VEC vaccine (Imlygic), Bacille Calmette-Guerin (BCG) vaccine, peptide or protein vaccines, interferon, or interleukin-2 (IL-2) directly into the melanoma; applying imiquimod cream; and chemotherapy (e.g., dacarbazine, temozolomide). For melanoma patient having mutations in the BRAF gene in the cancer cells, targeted therapy drugs such as vemurafenib (Zelboraf), dabrafenib (Tafinlar), trametinib (Mekinist), or cobimetinib (Cotellic) may also be used. For melanoma patient having changes in the C-KIT gene, targeted drugs such as imatinib (Gleevec) and nilotinib (Tasigna) may also be used.

Various embodiments provide the disclosed methods further include administering a therapeutic agent against the primary tumor or the metastases of that tumor. For example, a method for identifying subject having developed or a high likelihood of developing melanoma metastases further includes administering an effective amount of a drug selected from the group consisting of aldesleukin, binimetinib, encorafenib, cobimetinib, dabrafenib, dacarbazine, encorafenib, imlygic, recombinant interferon alfa-2b, ipilimumab, pembrolizumab, trametinib, nivolumab, peginterferon alfa-2b, pembrolizumab, vemurafenib, and a combination thereof to treat or reduce the severity of metastatic melanoma, primary melanoma, or both.

Symptoms

Various embodiments of one or more of the disclosed methods herein include a subject that has one or more symptoms of cancers. For example, some symptoms include skin changes, such as a new mole or a change in an existing mole and a sore that does not heal; breast changes, such as change in size or shape of the breast or nipple, change in texture of breast skin; a thickening or lump on or under the skin; hoarseness or cough that does not go away; changes in bowel habits; difficult or painful urination; problems with eating, such as discomfort after eating, a hard time swallowing, and changes in appetite; weight gain or loss with no known reason; abdominal pain; unexplained night sweats; unusual bleeding or discharge, including blood in the urine, vaginal bleeding, and blood in the stool; and feeling weak or very tired.

Some embodiments provide melanoma has one or more symptoms of a new, unusual growth or a change in an existing mole, spread of pigment from border of a spot into surrounding skin, redness or a new swelling beyond the border of the mole, and change in sensation such as itchiness, tenderness or pain.

Control Level and Exclusions

A reference or control is generally the value(s) of the same gene(s) or protein(s) as that the control is being compared to, where the control value(s) are obtained from a subject free from a cancer (e.g., melanoma); from a tissue sample free from the cancer (e.g., melanoma) of a subject; or from the primary tumor (e.g., melanoma) tissue of a subject that does not have the tumor (e.g., melanoma) reoccurrence and metastatic disease after local melanoma excision (e.g., shown over a course of time of about 1, 2, 3, 4, 5, 6, 7, 8, 9, 10 or more years; e.g., cured from the cancer). In other embodiments, a reference or control is the value(s) of a house-keeping gene or protein.

Some aspects of the methods provide one or more genes are not elevated in the primary cancer sample of the subject who does not have a high likelihood of developing or has not developed metastatic cancer; and these genes include those encoding lysyl oxidase (LOX), PIK3CD (phosphoinositide-3-kinase, catalytic, delta polypeptide), prostaglandin-endoperoxide synthase 1 (PTGS1), tumor necrosis factor receptor superfamily member 18 (TNFRSF18), Ras-related protein Rap-1A (RAP1A), alpha-actin-2 (ACTA2), vascular cell adhesion molecule 1 (VCAM-1), chromosome 10 open reading frame 54 (C10orf54), tyrosinase (TYR), receptor-type tyrosine-protein phosphatase kappa (PTPRK), Janus kinase 1 (JAK1), insulin-like growth factor 2 (IGF-2), protein melan-A (MLANA), tumor necrosis factor receptor superfamily member 14 (TNFRSF14), CD276, Mitogen-Activated Protein Kinase Kinase 2 (MAP2K2), Mitogen- Activated Protein Kinase Kinase Kinase 1 (MAP3K1), interleukin 8 (IL8), insulin-like growth factor 1 receptor (IGF1R), coagulation factor III (F3), and mothers against decapentaplegic homolog 7 (SMAD7).

Some embodiments provide the method of identifying subjects at risk of, or having developed, metastases from analyzing primary tumor samples includes detecting a higher expression level in mRNA, protein or both of only CXCL1, compared to a control level (e.g., obtained from a control subject or specimen, where the control subject can be a healthy or cured subject free from the tumor); and the method can further include administering a therapeutic agent to reduce the expression level of CXCL1, so as to treat or reduce the likelihood of metastases in the subject. Another embodiment provides the method of identifying subjects at risk of, or having developed, metastases from analyzing primary tumor samples includes detecting higher expression levels in mRNA, protein or both of only CXCL1 and CXCL2, compared to respective control levels (e.g., those obtained from a control subject or specimen, where the control subject can be a healthy or cured subject free from the tumor); and the method can further include administering a therapeutic agent to reduce the expression level of CXCL1, CXCL2 or both, so as to treat or reduce the likelihood of metastases in the subject. Another embodiment provides the method of identifying subjects at risk of, or having developed, metastases from analyzing primary tumor samples includes detecting higher expression levels in mRNA, protein or both of only CXCL1, CXCL2, CBL and CD276, compared to respective control levels (e.g., those obtained from a control subject or specimen, where the control subject can be a healthy or cured subject free from the tumor); and the method can further include administering a therapeutic agent to reduce the expression level of CXCL1, CXCL2, CBL, CD276 or a combination thereof, so as to treat or reduce the likelihood of metastases in the subject.

Microarray in Identifying Prognosis Markers

Also provided is a method of identifying one or more markers associated with metastases of a tumor in a population of subjects at the time of developing primary tumor, where a primary tumor biopsy or specimen of each subject is analyzed for the levels of immune-modulating genes in a microarray assay, and a significantly higher or lower level of one or more genes from subjects who later develop metastatic disease, compared to the level from subject who do not later develop metastatic disease, indicates the one or more markers prognostic of metastases of the tumor.

In some embodiments, microarray analysis of gene expression profiles is performed on fresh biological samples. In other embodiments, microarray analysis of gene expression profiles is performed on paraffin-embedded biological samples. Generally, the microarray analysis of primary tumor samples includes hybridizing detectably labeled RNA of the biological sample in an oligonucleotide microarray chip, wherein the oligonucleotide microarray chip contains one or more oligonucleotides that bind target genes, and quantifying the RNA amount of target genes in the biological sample via the detectable label. A detectable label includes, but is not limited to, a fluorescent protein, a gene encoding for a fluorescent protein, a luminescent protein, or a gene encoding for a luminescent protein.

Drug Development/Screening

Also provided is a method of identifying an agent for reducing the likelihood of melanoma reoccurrence or developing metastatic disease, which includes contacting a candidate agent with (1) CXCL1, (2) each of CXCL1 and CXCL2, or (3) each in the combination of CXCL1, CXCL2, CBL and CD276, and measuring the activity of CXCL1, in combination with CXCL2, further in combination with CXCL2, CBL and CD276, or receptors thereof, where a reduced level of the activity indicates the candidate agent reducing the likelihood of melanoma reoccurrence or developing metastatic disease.

An embodiment provides a method of screening for and using a candidate agent for treating, reducing the likelihood or severity of, or slowing the progression of metastases or reoccurrence of melanoma in a subject, which includes contacting the candidate agent with a melanoma cell line or tissue that expresses one or more of CXCL1, CXCL2, CBL and CD276, wherein after the contact a reduced activity or reduced expression in one or more of CXCL1, CXCL2, CBL, and CD276 compared to before the contact identifies a candidate agent for treating, reducing the likelihood or severity of, or slowing the progression of metastases or reoccurrence of melanoma.

Another embodiment provides a method of screening for and using a candidate agent for treating, reducing the likelihood or severity of, or slowing the progression of metastases or reoccurrence of melanoma in a subject, which includes or consists of (1) contacting the candidate agent with a melanoma cell line or tissue that expresses one or more of CXCL1, CXCL2, CBL and CD276, wherein after the contact a reduced activity or reduced expression in one or more of CXCL1, CXCL2, CBL, and CD276 compared to before the contact identifies a candidate agent for treating, reducing the likelihood or severity of, or slowing the progression of metastases or reoccurrence of melanoma; and (2) administering the identified candidate agent to a subject having higher expression levels of one or more of CXCL1, CXCL2, CBL and CD276 in a melanoma sample of the subject compared to those of a subject free from melanoma, of a skin tissue sample free from melanoma, or of a melanoma sample of a subject that does not have metastasis or reoccurrence of melanoma.

Yet another embodiment provides a method of screening for and using a candidate agent for treating, reducing the likelihood or severity of, or slowing the progression of metastases or reoccurrence of melanoma in a subject, which includes (1) contacting the candidate agent with a melanoma cell line or tissue that expresses one or more of CXCL1, CXCL2, CBL and CD276, wherein after the contact a reduced activity or reduced expression in CXCL1 compared to before the contact identifies a candidate agent for treating, reducing the likelihood or severity of, or slowing the progression of metastases or reoccurrence of melanoma; and (2) administering the identified candidate agent to a subject having or having had melanoma, wherein the subject has been diagnosed or made prognosis of melanoma metastasis with higher expression levels of one or more of CXCL1, CXCL2, CBL and CD276 in the melanoma sample compared to those obtained from a subject free from melanoma or free from melanoma metastases.

Exemplary assay methods for identifying such agents include biochemical assays (e.g., western blotting, enzyme-linked immunosorbent assay), cell functional analysis, ex vivo functional assay and in vivo assay.

Examples

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Methods

Thirty-seven patients with primary melanoma and no metastases underwent surgical excision of the primary lesion by a surgeon. All patients had biopsy-proven melanoma prior to resection. There were 37 patients who had residual, visible disease after biopsy and prior to wide local excision. These patients were followed prospectively for a median of 38 months (range 1-144 months).

Fresh frozen tissue samples of the primary wide local excision specimens from these 37 patients were taken and preserved in RNAlater (Qiagen-Hilden, Germany) followed by cryopreservation in liquid nitrogen. The specimens were securely de-identified through a centralized database. All samples were confirmed to contain >95% tumor cells. Using the Qiagen RNeasy Mini Kit, RNA was extracted from the frozen tissue samples. The concentration of RNA was measured by Nanodrop Spectrophotometer (Nanodrop Products-Wilmington, Del.) and the quality determined by the Bioanalyzer 2100 (Agilent Technologies-Santa Clara, Calif.). The RNA was labeled using the Quick AMP Labeling Kit (Agilent Technologies) and purified on RNeasy columns (Qiagen). Hybridization was performed by applying each sample (e.g., containing 1 µg of RNA) to the Agilent Human 44K 60-mer oligonucleotide microarray chip, a technology that relies on dual-color analysis. The samples were applied to slides which were incubated at 60 degrees Celsius for 16-17 hours, washed per Agilent protocol, then covered by ozone barrier immediately. The slides were run through the Agilent Scanner (G2565CA). Agilent Feature Extraction Software (version 9) was used to quantify the intensity of fluorescent images. cDNA was generated from the primary tumor specimens and used for microarray analysis to determine the types of immunoregulatory genes and their upregulation/downregulation in melanoma. The patients were followed up for recurrence/metastasis. Differential gene expressions of 79 immunomodulatory genes were compared between patients who developed distant metastases and those who did not. Microarray gene expression was processed with quantile normalization and log 2 transformation. Because of missing data from five genes in the microarray set, the differential expression of the remaining 74 genes was analyzed and compared between the metastatic and non-metastatic groups using Student's t-test. The significance level of differential expression was set to a false discovery rate (FDR) of 0.05. To assess the capacity for predicting distant metastases, a univariate logistic regression model was performed to determine the predictive power of each demographic factor, tumor characteristic, and expression of the four genes with the greatest upregulation from the microarray analysis. Multivariable logistic regression with stepAIC was performed on the significant variables from the univariate analysis to identify significant predictors of distant metastases. The Kaplan-Meier method was used to estimate the overall survival between groups using 90% quantile separation of CXCL1 expression levels because it was the unique significant predictor emerging from StepAIC procedure. Logrank testing was used to compare the difference in survival. Area under the curve, sensitivity, specificity, positive and negative predictive values were calculated for CXCL1 as a predictive biomarker.

Results

Of the 37 patients with primary cutaneous melanoma, six (16% of the cohort) developed distant metastases during the study period. Patient demographics and clinical characteristics were compared between groups using Student's t-test, Fisher's exact test, and Mann-Whitney u-test set at a significance level of 0.05 (Table 1). There was no statistically significant difference between the patients who developed distant metastases and those who did not with respect to age, gender, site of primary tumor, Breslow thickness, sentinel lymph node positivity, mitotic index, regression, or length of follow-up (Table 1). The majority of patients from both groups were ≥60 years old with primaries of the trunk and extremities. Ulceration was the only characteristic significantly different between groups with the group that developed metastases demonstrating a higher rate of ulceration (50% vs 13%, p=0.05). Two patients had metastases to the lungs, three had distant subcutaneous metastases and one had diffuse metastatic disease. Three of the patients were diagnosed with distant metastases within two years of primary diagnosis and the other three patients were diagnosed 4-5 years after initial diagnosis.

After multivariate analysis, four immunomodulatory genes were found to be overexpressed in the group of patients that eventually developed distant metastases. These four genes include CXCL1, CXCL2, CD276, and CBL, which all have varying roles in the immune cascade. CBL, a proto-oncogene relevant to ubiquitin pathways, was overexpressed in the metastatic group with differential expression fold change (DEFC) of 1.15, p=0.01. The CD276 gene, which activates T-cell immunity, was overexpressed with DEFC 1.16, p=0.04. CXCL1 and CXCL2, which encode chemokines regulating growth and inflammation, were overexpressed in the metastatic group with DEFC of 2.51 and 1.68 respectively, p<0.001 and p=0.01.

On univariate analysis, the following factors were predictive of developing distant metastases: ulceration (p=0.05) and overexpression of CXCL1 (p=0.01), CXCL2 (p=0.04), CD276 (p=0.05), and CBL (p=0.03). However, after multivariable analysis with StepAIC, only CXCL1 remained significant as a predictor of distant metastases (p=0.01, Table 2). As a predictive biomarker, CXCL1 demonstrated an area under the curve (AUC) of 0.80. The sensitivity and the specificity of CXCL1 for prediction of metastases were 0.67 and 0.97, respectively. The positive predictive value was 0.80 and the negative predictive value was 0.94. (Table 3; FIGS. 3-6) MET refers to the development of metastatic disease during the follow-up of patient after excision of the primary melanoma.

Figure 8:
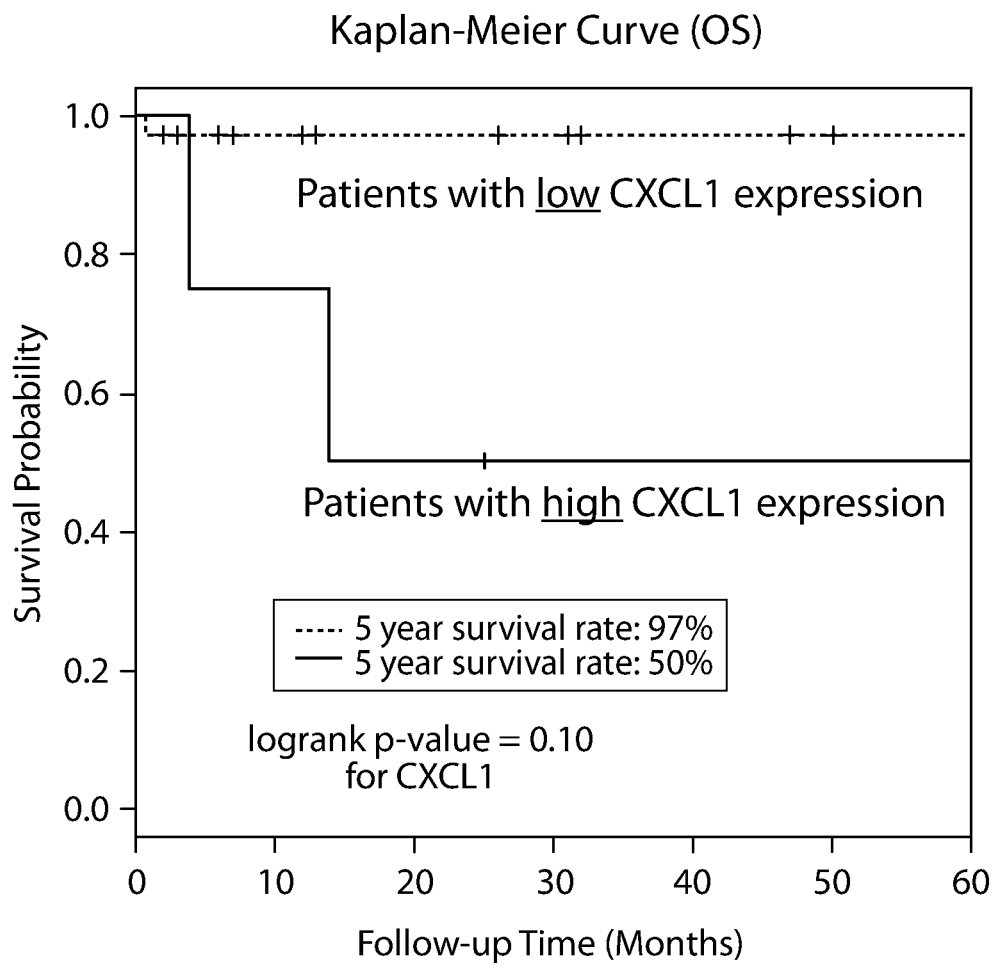
FIG. 8 is a Kaplan-Meier curve comparing the overall survival (OS) of melanoma patients with low CXCL1 expression (generally the upper curve: with a survival rate of 97% at 5 years) and that of melanoma patients with high CXCL1 expression (generally the lower curve: with survival rate of 50% at 5 years). "High" level of CXCL1 in this graph refers to at least 2.5 times higher than background/control levels of mRNA expression.

The 5-year survival for CXCL1 overexpression was 50% compared to 97% for those who under-expressed CXCL1, though this did not reach statistical significance (p=0.1). (FIG. 8: median overall survival for the former=64 months).

Figure 2:
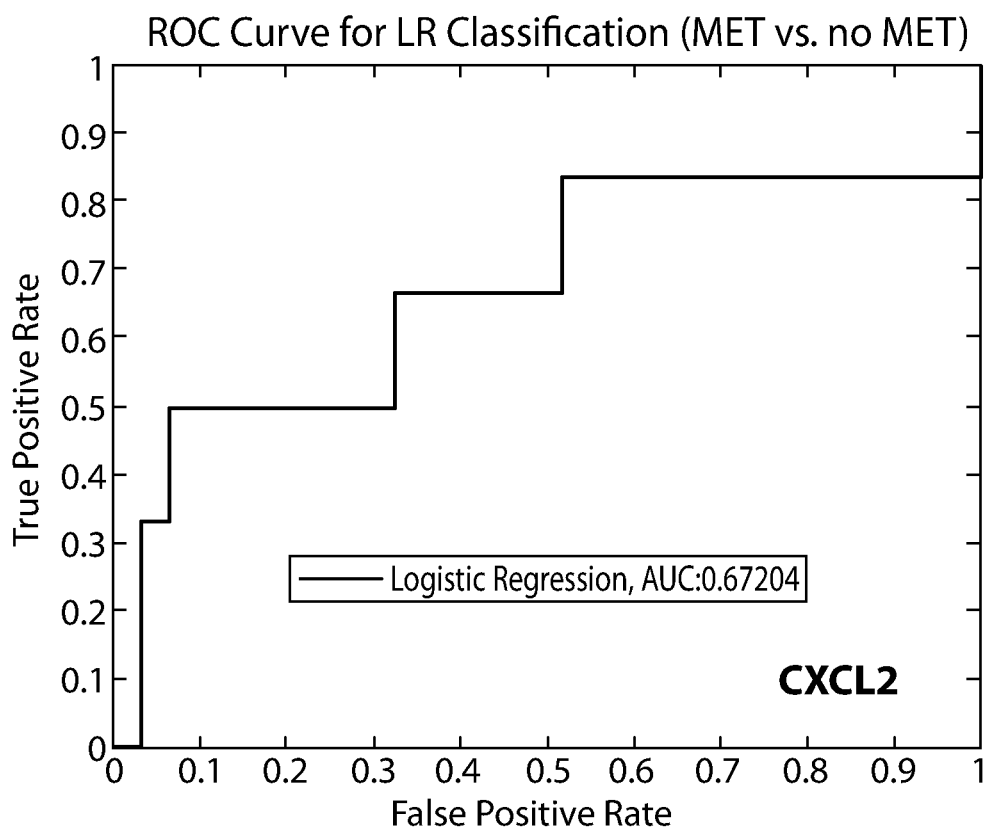
Figure 3:
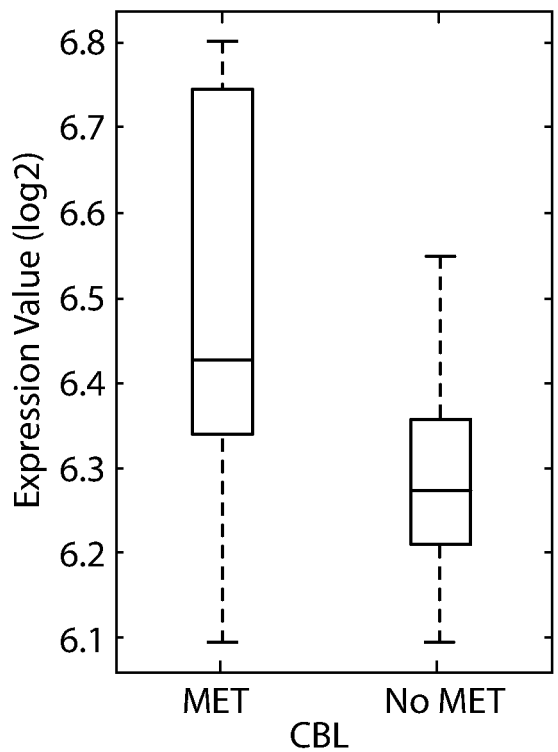
FIGS. 3-6 depict the expression values (log 2) of immune modulating genes, CBL (FIG. 3), CD276 (FIG. 4), CXCL2 (FIG. 5) and CXCL1 (FIG. 6) from primary melanoma samples in patients who developed metastasis and in patients who did not develop metastasis.
Figure 4:
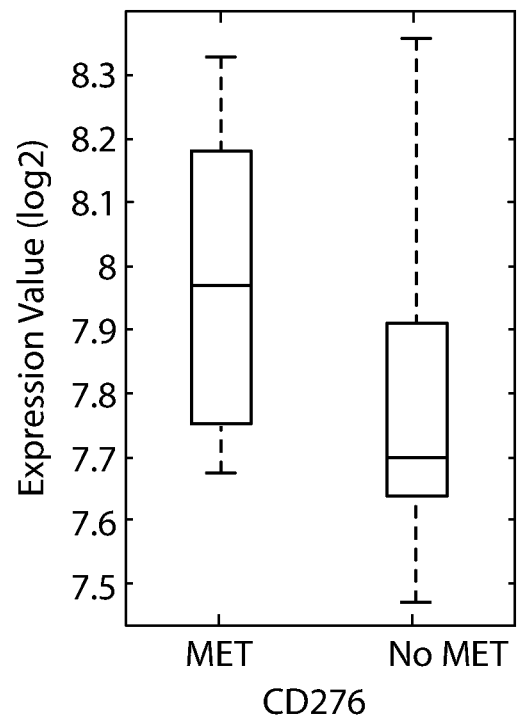
Figure 5:
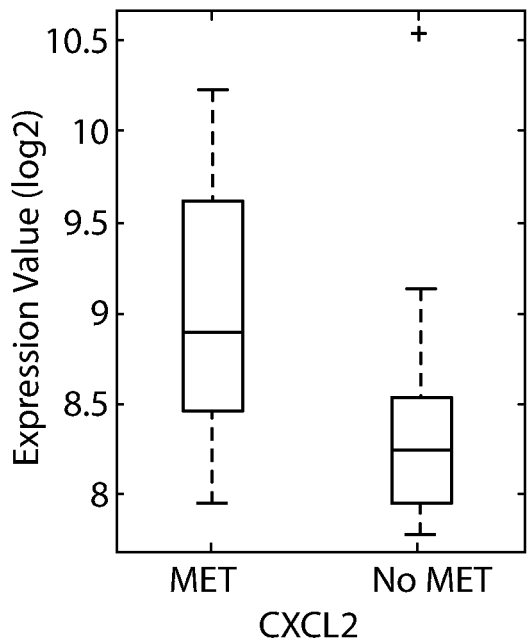
Figure 6:
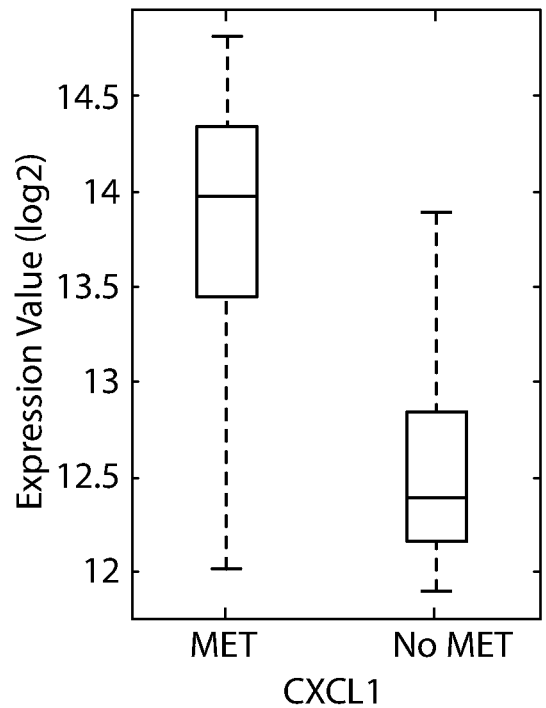
Figure 7:
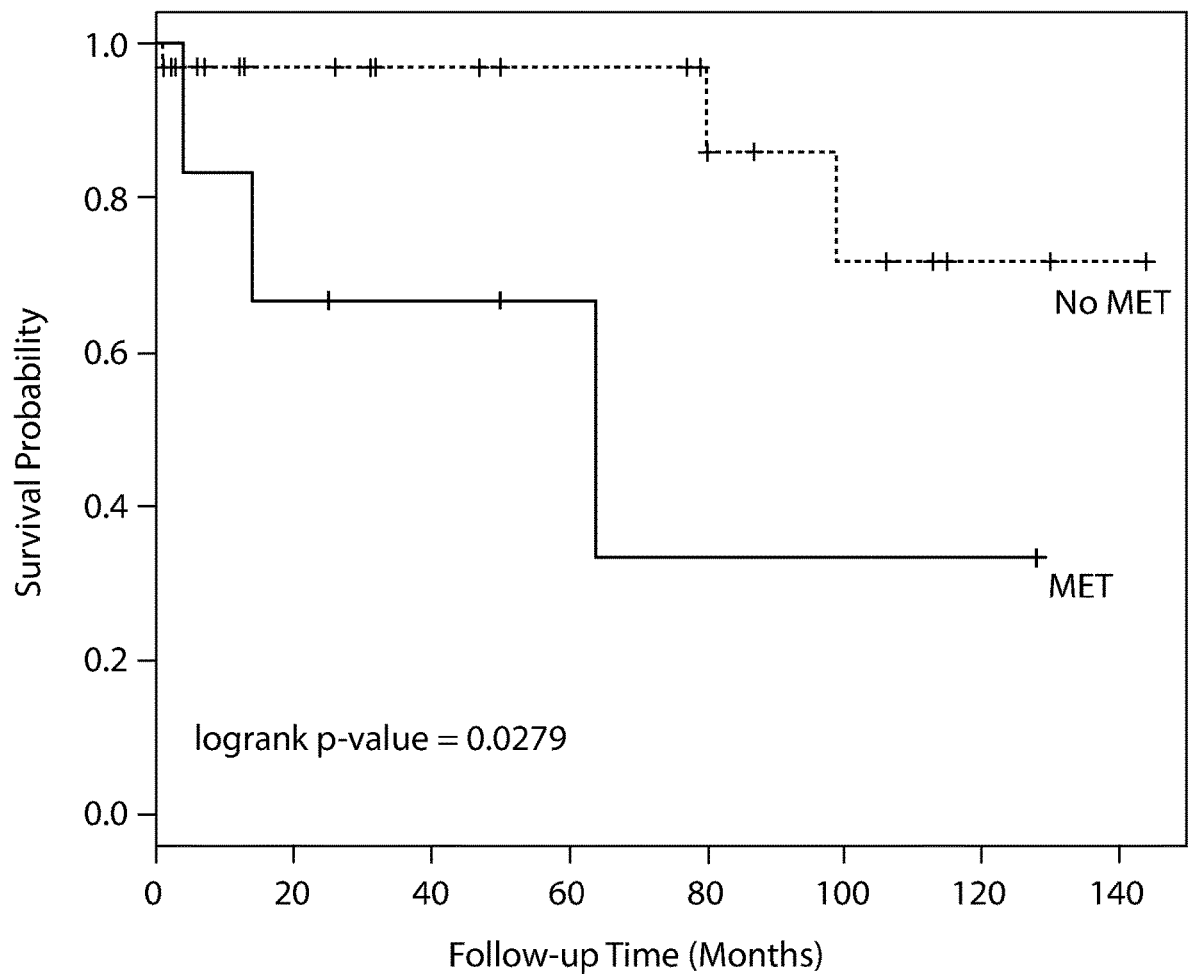
FIG. 7 is a Kaplan-Meier curve comparing the overall survival (OS) of melanoma patients who developed metastasis (MET) and that of melanoma patients who did not develop metastasis (No MET).

FIGS. 1 and 2 show the receiver operating characteristic curve (ROC curve) for CXCL1 and CXCL2, respectively.

The significant differentially expressed genes were selected to fit a logistic regression model for prediction of different groups. Using CXCL1 and CXCL2 genes to predict MET vs. no MET has an AUC of 0.8172. Since CXCL1 and CXCL2 are highly correlated, using CXCL1 the AUC can reach 0.80108. The gene profiles were highly predictive of patient outcome, and could be used as an alternative to surgical staging of lymph nodes.

TABLE 1

Clinical and Pathologic Characteristics

| Variables | Patients (MET) | Patients (No MET) | p-value |
|---|---|---|---|
| Total | 6 | 31 | |
| Age | | | 0.15 |
| Under 60 | 0 (0%) | 12 (39%) | |
| 60 and above | 6 (100%) | 19 (61%) | |
| Gender, no (%) | | | 0.06 |
| Male | 6 (100%) | 16 (52%) | |
| Female | 0 (0%) | 15 (48%) | |
| Site of Specimen, no (%) | | | 1.00 |
| Head and neck | 2 (33%) | 9 (29%) | |
| Trunk/Extremities | 4 (67%) | 22 (71%) | |
| Thickness of Primary Tumor (mm), median [Range] | 2.1 [0.15.5] | 1.05 [0.23-10] | 0.66 |
| Follow-up (Month), median[Range] | 38[4-128] | 26[1-144] | 0.56 |
| Lymph Node Metastasis, no. | | | 0.18 |
| Yes | 2 (33%) | 3 (10%) | |
| No | 4 (67%) | 28 (90%) | |
| Mitosis, no.(%) | | | 0.33 |
| Low | 2 (33%) | 21 (68%) | |
| High | 3 (50%) | 10 (32%) | |
| Unknown | 1 (17%) | 0 (0%) | |
| Ulceration, no.(%) | | | 0.05 |
| Yes | 3 (50%) | 4 (13%) | |
| No | 2 (33%) | 26 (84%) | |
| Unknown | 1 (17%) | 1 (3%) | |
| Regression, no.(%) | | | 0.56 |
| Yes | 0 (0%) | 7 (23%) | |
| No | 5 (83%) | 23 (74%) | |
| Unknown | 1 (17%) | 1 (3%) | |

Data are expressed as n (%)
Low Mitosis defined as O mm/2, High mitosis equal to or greater than 1 mm/2

TABLE 2

Factors Predictive of Developing Metastases

| Variable | Univariate Analysis p-value | Multivariate Analysis p-value |
|---|---|---|
| Age | 0.55 | NS |
| Gender | 0.99 | NS |
| Thickness | 0.65 | NS |
| Ulceration | 0.05 | NS |
| Positive LN | 0.15 | NS |
| Primary site | 0.83 | NS |
| CXCL1 | 0.01 | 0.01 |
| CXCL2 | 0.04 | NS |
| CD276 | 0.05 | NS |
| CBL | 0.03 | NS |

Each variable as compared between the metastatic and non-metastatic group.
Age defined as Under 60 v 60 and above. Thickness in mm. Primary site as Head & Neck v. Trunk/Extremities .
"NS," not significant

TABLE 3

Prediction of metastasis.

| Bio-marker | AUC | Sensi-tivity | Specificity | Accuracy | Positive Predictive Value (PPV) | Negative Predictive Value (NPV) |
|---|---|---|---|---|---|---|
| CXCL1 | 0.80 | 0.67 | 0.97 | 0.92 | 0.8 | 0.94 |
| CXCL2 | 0.67 | 0 | 0.97 | 0.81 | 0 | 0.83 |
| CBL | 0.69 | 0.33 | 1 | 0.89 | 1 | 0.89 |
| CD276 | 0.58 | 0 | 0.97 | 0.81 | 0 | 0.83 |

*For CXCL2 and CD276, the sensitivity and positive predictive value are 0, i.e., the two genes cannot predict true positives. But they predict true negatives given their specificity value and the negative predictive value (NPV).

CXCL1, CXCL2, CBL, and CD276 were overexpressed immunomodulatory genes present in primary melanoma that were strongly associated with development of metastatic disease. Identification of their presence, particularly CXCL1, in the primary tumor could be used to predict who is at risk of future metastatic disease and thereby identify patients who might benefit from immunotherapy.

Testing CXCL1, CXCL2, CBL, and CD276 expression can identify patients at risk of developing metastatic melanoma. Identifying the expression of these genes can better predict prognosis than prior markers. Patients with overexpression might benefit from immunotherapy.

Table 4 below shows the differential expression fold change of various genes in lymph node metastases (LN-MET) patients vs. non-LNMET patients.

TABLE 4

Differential expression fold change of genes in LNMET patients vs non-LNMET.

| GeneName | DE FoldChange (LNMET vx. No LNMET) (5 vs. 32) | p-value |
|---|---|---|
| LOX | 0.66 | 0.00 |
| PIK3CD | 1.43 | 0.00 |
| PTGS1 | 0.62 | 0.00 |
| TNFRSF18 | 0.62 | 0.00 |
| RAP1A | 0.73 | 0.01 |
| ACTA2 | 0.71 | 0.01 |
| VCAM1 | 0.62 | 0.01 |
| C10orf54 | 0.77 | 0.01 |
| TYR | 1.48 | 0.01 |
| PTPRK | 0.78 | 0.01 |
| JAK1 | 0.84 | 0.01 |
| IGF2 | 0.77 | 0.01 |
| MLANA | 1.52 | 0.02 |
| TNFRSF14 | 1.28 | 0.02 |
| CD276 | 1.19 | 0.03 |
| MAP2K2 | 1.26 | 0.03 |
| MAP3K1 | 0.79 | 0.03 |

TABLE 4-continued

Differential expression fold change of genes in LNMET patients vs non-LNMET.

| GeneName | DE FoldChange (LNMET vx. No LNMET) (5 vs. 32) | p-value |
|---|---|---|
| IL8 | 1.97 | 0.03 |
| IGF1R | 1.18 | 0.04 |
| F3 | 0.72 | 0.04 |
| SMAD7 | 0.87 | 0.04 |

The AUC for ACTA2 was 0.8563.

TABLE 5

Prediction of metastasis to distant site

| Biomarker | AUC | Sensitivity | Specificity | Accuracy | Positive Predictive Value (PPV) | Negative Predictive Value (NPV) |
|---|---|---|---|---|---|---|
| ACTA 2 | 0.86 | 0.2 | 0.97 | 0.86 | 0.5 | 0.89 |

The combination of IL1A, PTPRK and ClarkLevel provides an AUC of 0.8125 for predicting LNMET+MET vs. no LNMET+MET. "LNMET+MET" refers to lymph node metastases from melanoma patient; and "no LNMET+MET" refers to no lymph node metastases from melanoma patient.

The expressions of a few selected immunomodulatory genes in the primary melanoma tumors are different in patients who develop distant metastases, compared to those who do not develop distant metastases. Four genes were significantly overexpressed in the primary specimens of those who developed distant metastases: CXCL1, CXCL2, CD276, and CBL. These genes have varying roles in cell signaling, and have appeared elsewhere as important mediators in cancer, including melanoma. Of these four genes, CXCL1 showed 2.51 times greater expression in the primary specimens of the group that developed metastases (p<0.001). Furthermore, it was the most robust factor in multivariable analysis at predicting metastases (p=0.01) and demonstrated an excellent AUC at 0.80. With high sensitivity, specificity, positive and predictive value, CXCL1 is a potential independent biomarker in primary melanoma.

CXCL1 and CXCL2 are genes on chromosome that encode cytokines involved in growth and inflammation. The chemokines they encode are secreted by macrophages for neutrophil recruitment in the presence of necrotic cells. Both exert their signal through the same receptor, CXCR2. CD276 belongs to the B7/CD28 family of immune-regulatory proteins. C-CBL is an E3 ubiquitin ligase that regulates nuclear B-catenin and angiogenesis via TKR and Wnt-signaling. The CBL family participates in the MAPK pathway and targets TKR for degradation.

There are several strengths of the present study. First, all patients had visible, residual melanoma after biopsy, which is not commonly the case because preoperative biopsy often leaves little to no intact tumor before surgery. Second, data on these patients was collected prospectively and the long follow-up revealed a subset who developed distant metastases. Third, by preselecting a list of 79 immunomodulatory genes for analysis, the odds of a false discovery rate (FDR) were substantially reduced to 0.7%. Had the whole genome been analyzed, then 1000 genes might emerge relevant by random chance.

To applicant's knowledge, this is the first study to analyze the prediction of distant metastases based on the primary tumor, and uncover four genes, particularly CXCL1 as informative of the risk of distant disease. This allows for the use of primary tumor microenvironment for risk stratification and identify candidates for immunotherapy earlier in the disease course.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

What is claimed is:

1. A method of detecting and identifying a likelihood of metastasis from primary melanoma tumor in a subject with a primary melanoma cancer that has not metastasized for a therapy and administering the therapy to the subject, comprising:

detecting an expression level of chemokine C—X—C motif ligand (CXCL) 1 (CXCL1) in a biological sample obtained from the subject as being above a control level, wherein the biological sample comprises melanoma tumor cells and is obtained when the melanoma cancer has not metastasized, wherein the control level is an expression level of CXCL1 in a primary melanoma tissue obtained from one or more subjects who did not develop metastasis of melanoma in one to 144 months after the primary melanoma tissue was obtained; and identifying the subject as having likelihood of metastasis of the primary melanoma tumor based on understanding that a higher expression level of CXCL1 in a primary melanoma sample than the control level indicates a likelihood of metastasis as compared to not having the higher expression level of CXCL1 in the primary melanoma sample;

administering a therapy to the subject detected with the expression level of CXCL1 above the control level to reduce the likelihood of metastasis, wherein the therapy comprises Sch-527123, an anti-CXCL1 antibody, repertaxin, ladarixin, AZD5069, Cpd 19, Sch-527123, SB272844, SB-656933, P0057390, P0087798, P0057390, enoblituzumab, or a combination thereof.

2. The method of claim 1, wherein the therapy comprises Sch-527123.

3. The method of claim 1, wherein the therapy comprises an anti-CXCL1 antibody.

4. The method of claim 1, further comprising performing sentinel lymph node biopsy with the subject to detect presence of lymph node metastasis, and wherein the therapy comprises adjuvant treatment, immunotherapy, radiation, or chemotherapy.

5. The method of claim 1, wherein the method further comprises surgically removing the melanoma tissue from the subject.

6. The method of claim 1, wherein the control level is an average expression level of CXCL1 in the primary melanoma tissue obtained from the subjects who did not develop metastasis of the melanoma in the one month to 144 months after the primary melanoma tissue was obtained.

7. The method of claim 1, wherein the detection comprises:

hybridizing detectably labeled RNA of the biological sample in an oligonucleotide microarray chip, wherein the oligonucleotide microarray chip comprises an oligonucleotide that binds CXCL1; and quantifying an RNA amount of the CXCL1 in the biological sample via the detectable label.

8. The method of claim 7, wherein the oligonucleotide microarray chip further comprises an oligonucleotide that binds CXCL2, and the quantification further quantifies an RNA amount of the CXCL2.

9. The method of claim 7, wherein the oligonucleotide microarray chip further comprises an oligonucleotide that binds CXCL2, an oligonucleotide that binds E3 ubiquitin-protein ligase CBL (CBL), and an oligonucleotide that binds cluster of differentiation 276 (CD276), and the quantification further quantifies an RNA amount of the CXCL2, an RNA amount of the CBL, and an RNA amount of the CD276.

10. The method of claim 1, wherein an RNA amount of the CXCL1 in the biological sample has a differential expression fold change (DEFC) of at least 2.51 compared to the control level.

11. The method of claim 1, wherein the detection further detects an expression level of CXCL2 in the biological sample as being above a respective control level, wherein the respective control level is obtained from one or more subjects who have not developed metastasis of melanoma cancer in the past one month to 144 months, or who are free or cured of melanoma cancer.

12. The method of claim 1, wherein the detection further detects expression levels of CXCL2, CBL, and CD276 in the biological sample as being above respective control levels, wherein the respective control levels are obtained from one or more subjects who have not developed metastasis of melanoma cancer in the past one month to 144 months, or who are free or cured of melanoma cancer.

13. The method of claim 11, wherein an RNA amount of the CXCL2 in the biological sample has a DEFC of at least 1.68 compared to the respective control level.

14. The method of claim 12, wherein an RNA amount of the CBL in the biological sample has a DEFC of at least 1.15 compared to the respective control level, and an RNA amount of the CD276 in the biological sample has a DEFC of at least 1.16 compared to the respective control level.

* * * * *